(12) United States Patent
Hwu et al.

(10) Patent No.: US 6,348,454 B1
(45) Date of Patent: Feb. 19, 2002

(54) SYNTHESES OF NEW ISODETHIAAZACEPHEMS AND ISODETHIAAZACEPHAMS, AND USE AS POTENT ANTIBACTERIAL AGENTS

(75) Inventors: Jih Ru Hwu; Shwu-Chen Tsay, both of Taipei (TW); Shahram Hakimelahi, Edmonton (CA)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/310,270

(22) Filed: May 12, 1999

(51) Int. Cl.[7] .................. C07D 487/04; A61K 31/4985; A61P 31/04
(52) U.S. Cl. ................... 514/210.05; 540/205; 540/364
(58) Field of Search ...................... 540/205; 514/210.05

(56) References Cited

PUBLICATIONS

Jih Ru Hwu et al., "Syntheses of New Isodethiaazacephems as Potent Antibacterial Agents", J. Med. Chem., 1998, Nov., 41(24):4681–4685.

Hwu, ECHET '98: Electron. Conf. Het. Chem. http://www.ch.ic.ac.uk/ectoc/echet98/pub/026/index.htm, Jun. 1998.*
Hakimelahi, Helv. Chem Acta 79, 813, 1996.*

* cited by examiner

Primary Examiner—Mark L Berch
(74) Attorney, Agent, or Firm—Fish & Richardson P.C.

(57) ABSTRACT

An isodethiaazacephem derivative having the following formula (I):

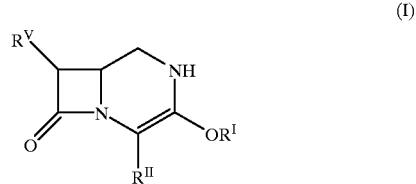

wherein $R^I$ is hydrogen or $-SO_2R^{III}$; $R^{II}$ is $-CO_2R^{IV}$ or $-SO_2R^{III}$ in which $R^{III}$ is a hydrogen, C1–C6 alkyl, aralkyl having a total carbon number of 7–12, aryl, or a halogenated C1–C6 alkyl; and $R^{IV}$ is a hydrogen, C1–C6 alkyl, aralkyl having a total carbon number of 7–12 or aryl; and $R^V$ is a substituted acetamido radical.

34 Claims, No Drawings

SYNTHESES OF NEW ISODETHIAAZACEPHEMS AND ISODETHIAAZACEPHAMS, AND USE AS POTENT ANTIBACTERIAL AGENTS

FIELD OF THE INVENTION

The present invention is related to syntheses of novel isodethiaazacephems and isodethiaazacephams, and their use as an potent antibacterial agent, and in particular isodethiaazacephems and isodethiaazacephams having an effective leaving group which can undergo an enzyme-initiated elimination process, so that the antibacterial activity thereof can be enhanced.

BACKGROUND OF THE INVENTION

β-Lactam antibiotics exert certain biological activity by acylating serine residues of transpeptidases so that the cross-linking of peptidoglycans does not take place [Waxman, D. J.; Strominger, J. L. Sequence of Active Site Peptides from the Penicillin-sensitive D-Alanine Carboxypeptidase of *Bacillus Subtilis*. *J. Biol. Chem.* 1980, 255, 3964–3976; FrÈre, J. M.; Nguyen-DistÈche, M.; Coyette, J.; Joris, B. Mode of Action: Interaction with the Penicillin Binding Proteins. In *The Chemistry of β-Lactams*; Page, M. I., Ed.; Blackie Academic & Professional: New York, 1992; pp 148–197]. As shown in Scheme 1, ring opening of the β-lactam nucleus would occur when cephalosporins (1) react with enzymes responsible for the cell wall synthesis of bacteria. Consequently, the substituent at the C-3' position is liberated [Boyd, D. B. Elucidating the Leaving Group Effect in the β-Lactam Ring Opening Mechanism of Cephalosporins. *J. Org. Chem.* 1985, 50, 886–888; Boyd, D. B.; Lunn, W. H. W. Electronic Structures of Cephalosporins and Penicillins. 9. Departure of a Leaving Group in Cephalosporins. *J. Med. Chem.* 1979, 22, 778–784; Faraci, W. S.; Pratt, R. F. Elimination of a Good Leaving Group from the 3'-Position of a Cephalosporin Need Not Be Concerted with β-Lactam Ring Opening. *J. Am. Chem. Soc.* 1984, 106, 1489–1490; Page, M. L.; Proctor, P. Mechanism of β-Lactam Opening in Cephalosporins. *J. Am. Chem. Soc.* 1984, 106, 3820–3825; Grabowski, E. J. J.; Douglas, A. W.; Smith, G. B. Ammonolysis of Cephalosporins: $^{13}C$ NMR Characterization of the Intermediates from β-Lactam Ring Cleavage Prior to Loss of the 3'-Group. *J. Am. Chem. Soc.* 1985, 107, 267–268]. When the eliminated species possesses excellent leaving ability, cephalosporins (1) may exhibit profound antibacterial activity.

Scheme 1
The Mode of Action of Cephalosporins with Transpeptidases

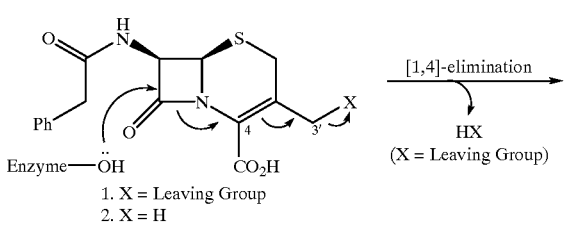

1. X = Leaving Group
2. X = H

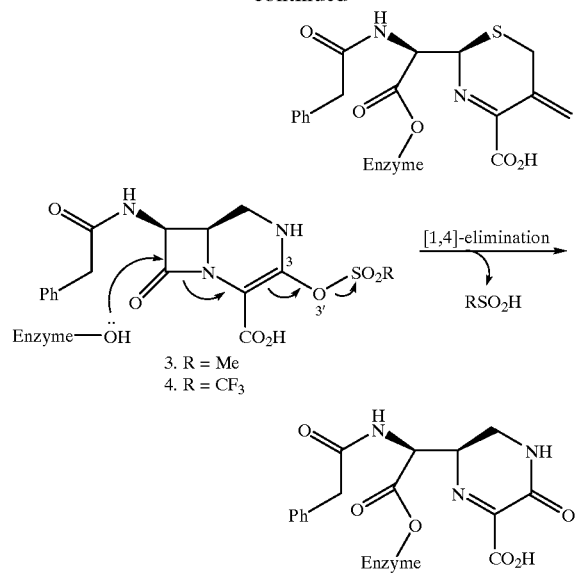

3. R = Me
4. R = $CF_3$

SUMMARY OF THE INVENTION

Accordingly, we designed and synthesized unprecedented isodethiaazacephems having the following formula (I):

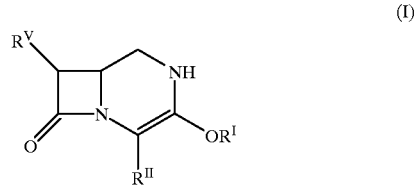

(I)

wherein $R^I$ is hydrogen or $-SO_2R^{III}$, preferably $-SO_2R^{III}$; $R^{II}$ is $-CO_2R^{IV}$ or $-SO_2R^{III}$, preferably $-CO_2R^{IV}$; and $R^V$ is a substituted acetamido radical;
wherein $R^{III}$ is a hydrogen, C1–C6 alkyl, aralkyl having a total carbon number of 7–12, aryl, or a halogenated C1–C6 alkyl; and $R^{IV}$ is a hydrogen, C1–C6 alkyl, aralkyl having a total carbon number of 7–12 or aryl.

We believe that the sulfone moiety, $-SO_2R^{III}$, at the O—3' position of (I) could act as an effective leaving groups, and thus further enhance the antibacterial activity in comparison with that of the parent 3-(hydroxy) isodethiaazacephem ($R^I$ is hydrogen).

Recognizing the feasibility of 1,4-elimination in β-lactam antibiotics as shown in Scheme 1, we also synthesized novel isodethiaazacephams having the following formula (II):

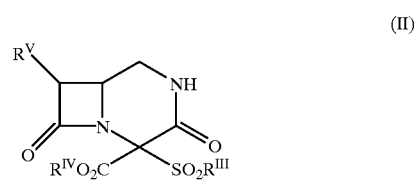

(II)

wherein $R^{III}$, $R^{IV}$ and $R^V$ are defined as above.

The newly designed compound (II) bears a leaving group at the C-4 position; the [1,2]-elimination process could also be initiated by bacterial enzymes (See Scheme 2).

Preferably, $R^{III}$ in the formula (I) is C1–C6 alkyl or halogenated C1–C6 alkyl, more preferably —CH$_3$ or —CF$_3$, and most preferably, —CF$_3$.

Preferably, $R^{III}$ in the formula (II) is C1–C6 alkyl, and more preferably —CH$_3$.

Preferably, $R^{IV}$ in the formulas (I) and (II) is hydrogen.

Preferably, $R^{V}$ in the formulas (I) and (II) is phenylacetamido.

DETAILED DESCRIPTION OF THE PREFERRED EMBODIMENTS

The present invention provides new classes of β-lactams (i.e. isodethiaazacephems and isodethiaazacephams) possessing notable antibacterial activity. In the following preferred embodiments of the present invention, we synthesized compounds 3–17, in which compounds 3, 4, 9–12 and 17 are isodethiaazacephem derivatives, and compounds 5 and 16 are isodethiaazacepham derivatives. The reaction routs for the synthesis of these β-lactams are illustrated in Schemes 3–5. Compounds (±)-3, (±)-4 and (±)-5 shown as follows are prominent examples among the general structures (I) and (II):

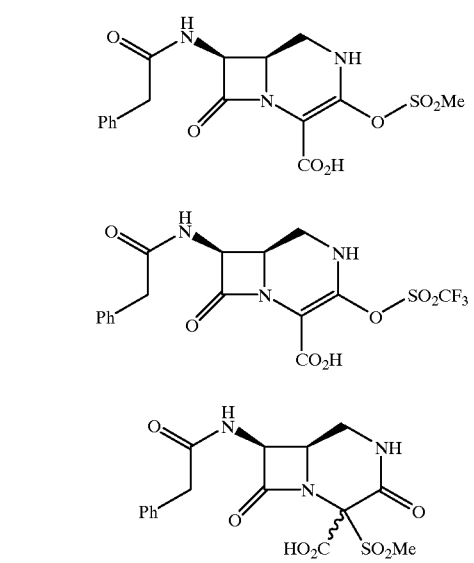

Scheme 2
The Mode of Action of a Cepham Sulfone with Transpeptidases

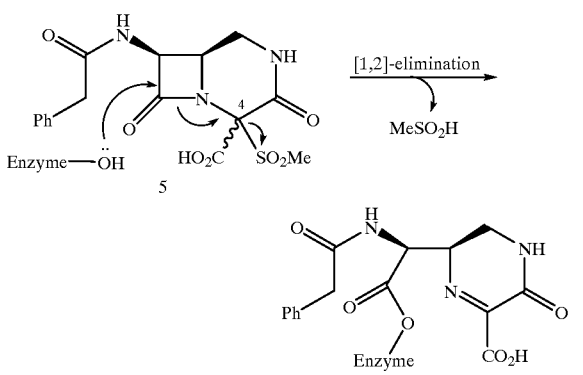

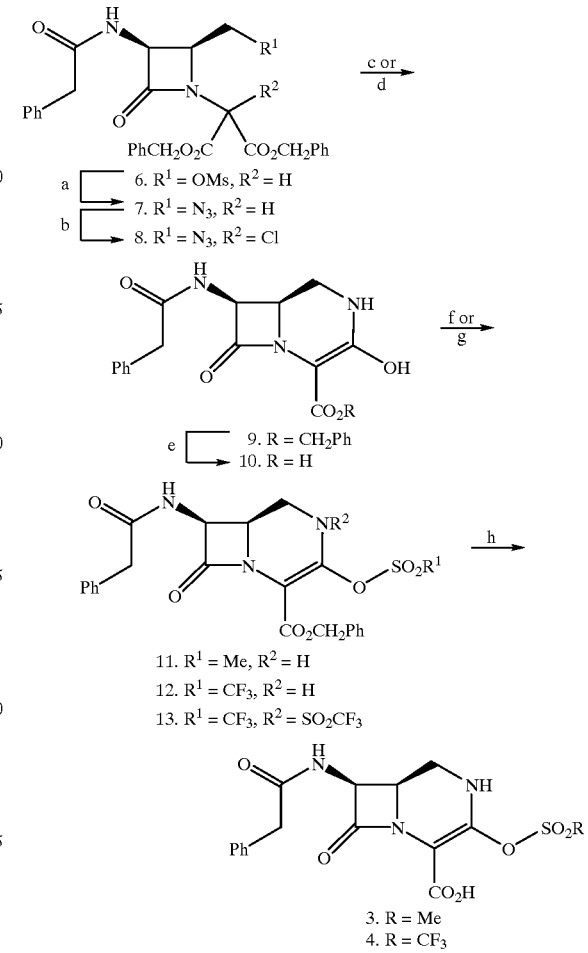

Reagents: (a) NaN$_3$, DMF, r.t. (90%); (b) CF$_3$SO$_2$Cl, Et$_3$N, CH$_2$Cl$_2$, 0° C.→r.t. (90%); (c) Pd/C, H$_2$, EtOAc, r.t., 7→9 (94%); (d) Pd/C, H$_2$, EtOAc, r.t., 8→9 (87%); (e) PdCl$_2$, H$_2$, EtOH, r.t. (50%); (f) MeSO$_2$Cl, pyridine, CH$_2$Cl$_2$, 15° C., 9→11 (45%); (g) CF$_3$SO$_2$Cl, pyridine, CH$_2$Cl$_2$, 15° C., 9→12 (30%)+13 (10%); (h) PdCl$_2$, H$_2$, EtOH, r.t., 11→3 (35%), 12→4 (30%).

Scheme 4

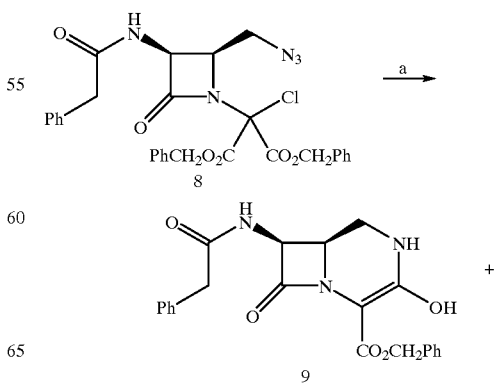

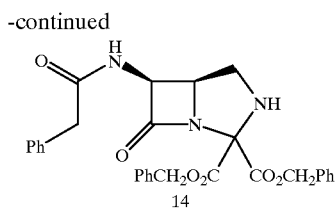

Reagents: (a) H$_2$S, Et$_3$N, CH$_2$Cl$_2$, r.t. (55%), 8→9 (15%)+14 (40%).

Scheme 5

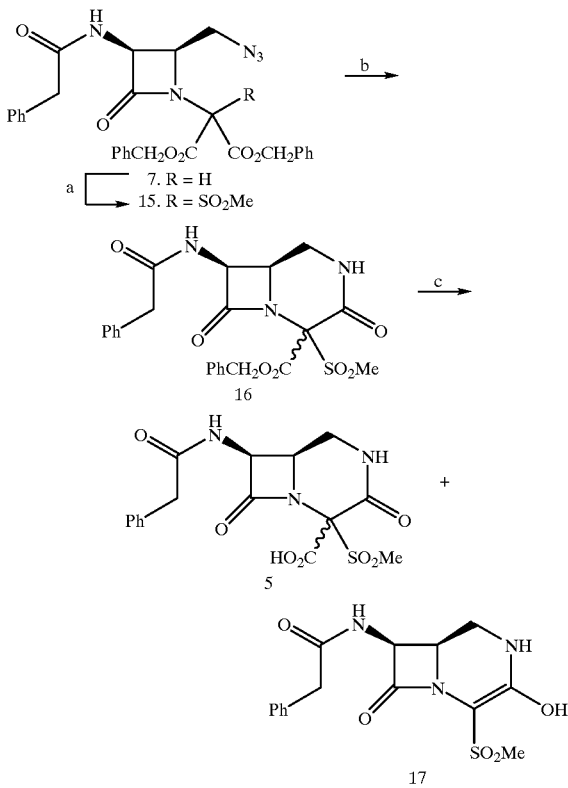

Reagents: (a) MeSO$_2$Cl, Et$_3$N, CH$_2$Cl$_2$, 0° C. (85%); (b) Pd/C, H$_2$, EtOAc, r.t. (90%); (c) PdCl$_2$, H$_2$, EtOH, r.t., 16→5 (20%)+17 (50%).

Synthesis of β-Lactams (±)-3, (±)-4, (±)-5, and (±)-10

For the synthesis of isodethiaazacephems (±)-3 and (±)-10, we treated racemic β-lactam mesylate 6 with NaN$_3$ in DMF at room temperature to give azido β-lactam 7 in 90% yield (Scheme 3) [Hakimelahi, G. H.; Just, G.; Ugolini, A. The Synthesis of an O-2-Isooxacephem. Helv. Chim. Acta 1982, 65, 1368–1373]. Catalytic hydrogenation of 7 by use of Pd/C and H$_2$ (30–35 psi) in EtOAc at room temperature resulted in the reduction of the azide moiety and spontaneous formation of isodethiaazacephem 9 in 94% yield. Debenzylation of 9 by use of PdCl$_2$ and H$_2$ (60 psi) in EtOH produced the target isodethiaazacephem (±)-10 in 50% yield.

An alternative way to obtain 9 from azido β-lactam 7 involved two steps. Chlorination of 7 with CF$_3$SO$_2$Cl in Et$_3$N and CH$_2$Cl$_2$ produced chloride 8 in 90% yield [Hakimelahi, G. H.; Tsay, S.-C.; Ramezani, Z.; Hwu, J. R. Syntheses of New Isocephems and Isodethiaoxacephems as Antimicrobial Agents. Helv. Chim. Acta 1996, 79, 813–819]. Consequent reduction of 8 by use of Pd/C and H$_2$ (30–35 psi) in EtOAc gave the desired compound 9 in 87% yield (Scheme 3). On the other hand, reaction of 8 with H$_2$S in Et$_3$N and CH$_2$Cl$_2$ produced a mixture of isodethiaazacephem 9 (15%) and isodethiaazapenam 14 (40%) as shown in Scheme 4.

We attached a sulfonyl group onto the cephem nucleus of 9 by mesylation with MeSO$_2$Cl in pyridine and CH$_2$Cl$_2$ to give the 3-mesyloxy β-lactam 11 in 45% yield (Scheme 3). It was then hydrogenated with PdCl$_2$ in EtOH at 60 psi of H$_2$ to produce the desired isodethiaazacephem (±)-3 in 35% yield. Moreover, we treated β-lactam 9 with CF$_3$SO$_2$Cl in pyridine and CH$_2$Cl$_2$ to afford a 3:1 mixture of trifluoromethanesulfonates 12 and 13 in 40% overall yield. Catalytic reduction of 12 with PdCl$_2$ in EtOH at 60 psi of H$_2$ gave the target isodethiaazacephem (±)-4 in 30% yield.

For the synthesis of isodethiaazacepham (±)-5 bearing a methylsulfonyl group at the C-4 position, we treated racemic azido β-lactam 7 with MeSO$_2$Cl in Et$_3$N and CH$_2$Cl$_2$ (Scheme 5). Sulfone 15, generated in 85% yield, was treated with H$_2$ (30–35 psi) and Pd/C in EtOAc to give bicyclic β-lactam 16 in 90% yield through sequential reduction and lactamization. Upon further reduction with H$_2$ at 60 psi in the presence of PdCl$_2$ and EtOH, compound 16 was converted to a mixture of the desired 4-substituted isodethiaazacepham (±)-5 in 20% yield and the decarboxylated product (±)-17 in 50% yield.

Solubility and Stability of β-Lactams (+)-3, (+)-4, (±)-5, (−)-10, and (±)-17 in Water We found that the solubility in water was 21 and 27 mg/mL for isodethiaazacephems (±)-3 and (±)-4, respectively; they were stable at physiological pH for six and four days, respectively. At pH 1.0, the β-lactam rings in (±)-3 and (±)-4 survived for ~4 and ~2 h, respectively; yet at pH 12, they were destructed within 5–10 min. On the other hand, 3-(hydroxy)isodethiaazacephem (±)-10 was highly soluble (35 mg/mL) in a phosphate buffer (0.10 M, pH 6.8) and was stable at least for two months.

Isodethiaazacepham (±)-5, highly soluble (32 mg/mL) in a phosphate buffer (0.10 M, pH 6.8), underwent decarboxylation gradually to give (±)-17 at room temperature within six days (Scheme 6). In a basic solution with pH 12, the decarboxylation also occurred to (±)-5 within 20 min; in an acidic solution with pH 1.0, the β-lactam ring in (±)-5 was destructed within 3 h. The β-lactam ring in (±)-17, however, was destructed at pH 1.0 within two days.

In another series of assays, we dissolved isodethiaazacephems (±)-3 and (±)-4 as well as isodethiaazacepham (±)-5 in distilled water (5.0 mg/mL). The pH value of the aqueous solutions was kept initially about 4.0 for (±)-3 and (±)-4, and about 2.0 for (±)-5. The pH values of the aqueous solutions of (±)-3 and (±)-4 changed to ~1 within three and two days, respectively. We found that the change in pH was accompanied by the destruction of the β-lactam rings in (±)-3 and (±)-4, as detected by IR spectroscopy, as well as the liberation of MeSO$_2$H and CF$_3$SO$_2$H, respectively. On the other hand, the pH value of an aqueous solution of (±)-5 changed from 2.0 to 6.0 within 5–6 days. This change was accompanied by the gradual production of (±)-17 through a decarboxylation process.

Biological Activity

We tested the antibacterial activity of the synthesized β-lactams (±)-3, (±)-4, (±)-5, (±)-10, (±)-11, (±)-12, and (±)-17, as well as the reference compounds cefotaxime [Muhtadi, F. J.; Hassan, M. M. A. In *Analytical Profiles of Drug Substances*; Florey, K., Ed.; Academic: New York, 1982; Vol. 11, pp 139–168; Wise, R.; Rollason, T.; Logan, M.; Andrews, J. M.; Bedford, K. A. HR 756, A Highly Active Cephalosporin: Comparison with Cefazolin and Carbenicillin. *Antimicrob. Agents Chemother.* 1978, 14, 807–811] penicillin G [Morris, J. J.; Page, M. I. Intra- and Intermolecular Catalysis in the Aminolysis of Benzylpenicillin. *J. Chem. Soc., Perkin Trans* 2 1980, 212–219], and 7-(β-phenylacetamido)-3'-desacetoxycephalosporanic acid (±)-2 [Page, M. L.; Proctor, P. Mechanism of β-Lactam Opening in Cephalosporins. *J. Am. Chem. Soc.* 1984, 106, 3820–3825] in vitro against five pathogenic microorganisms. The doses used were as high as 128 μg/mL. The results are summarized in Table 1.

TABLE 1

Minimal Inhibitory Concentrations[a] (μg/mL) of Synthetic β-Lactams as well as the Reference Compounds Cefotaxime, Penicillin G, and Cephalosporin (+)-2

| compounds | S. aureus FDA 209P | E. coli ATCC 39188 | S. typhi O-901 | Ps. aeruginosa 1101-75 | K. pneumoniae NCTC 418 |
|---|---|---|---|---|---|
| cefotaxime | 0.080 | 0.25 | 20.30 | 62.35 | 10.25 |
| penicillin G | 0.40 | 2.30 | >128 | >128 | >128 |
| (+)-2 | 0.64 | 13.13 | 24.50 | 100.0 | 2.98 |
| (±)-3 | 0.070 | 0.95 | 1.20 | 4.38 | 0.68 |
| (±)-4 | 0.010 | 0.090 | 0.68 | 1.15 | 0.24 |
| (±)-5 | 48.50 | 97.17 | 65.30 | 120.0 | 51.02 |
| (±)-10 | 29.50 | 94.68 | >128 | >128 | >128 |
| (±)-11 | >128 | >128 | >128 | >128 | >128 |
| (±)-12 | >128 | >128 | >128 | >128 | >128 |
| (±)-17 | >128 | >128 | >128 | >128 | >128 |

[a]Obtained by the serial broth dilution method [Pursiano, T. A.; Misiek, M.; Leitner, F.; Price, K. E. Effect of Assay Medium on the Antibacterial Activity of Certain Penicillins and Cephalosporins. Antimicrob. Agents Chemother. 1973, 3, 33–39]. The values represent the average of triplicate determinations.

Results from biological tests reveal promising antimicrobial activities for the enol sulfonate β-lactams (±)-3 and (±)-4. In comparison with the parent enol β-lactam (±)-10, the enol sulfonate β-lactams (±)-3 and (±)-4 exhibite much higher activity. Therefore, the antibacterial activity of (±)-3 and (±)-4 is enhanced substantially by possessing a potential leaving group at the O-3' position.

Moreover, the trifluoromethanesulfone unit in (±)-4 is a better leaving group than the methanesulfone unit in (±)-3. Thus, antibacterial activity is more potent for (±)-4 than (±)-3, as observed. The results indicate that the importance of mesylate and triflate functionalities at the C-3 position on the biological activity of cephalosporins. This is in agreement with our hypothesis regarding their mode of action in biological systems (Scheme 1).

A carboxyl group at the C-4 position of cephalosporins 1 is essential for recognition by the target enzymes, such as penicillin binding proteins (PBPs) [Neu, H. C. Structure-Activity Relationships: Biological. In *The Chemistry of β-Lactams*; Page, M. I., Ed.; Blackie Academic & Professional: New York, 1992; pp 101–128]. β-lactams (±)-3 and (±)-4 are substrates of PBPs. On the other hand, their benzyl ester derivatives (±)-11 and (±)-12, lack of a carbonxyl group at the C-4 position, do not exhibit antibacterial activity (Table 1) although they both possess excellent—$SO_2Me$ and —$SO_2CF_3$ leaving groups. Thus, both the chemical reactivity and the recognition capability of a substrate by the target enzymes are essential for its biological activity, as expected.

Isodethiaazacephams bearing a good leaving group at the C-4 group position can undergo an enzyme-initiated 1,2-elimination as shown in Scheme 2. We found that mesylated β-lactam (±)-5 indeed exhibites profound antibacterial activity (Table 1).

It is apparent that the 7-phenylacetamido group in the β-lactams (I) and (II) of the present invention may be replaced by various substituted acetamido groups used in the known antibacterial agents to further enhance the antibacterial activity thereof. Suitable substituted acetamido groups include (but limited to) phenoxyacetamido and the following side chains of cephotetan, cefotaxime, cefotoxin, moxalactam, cefazolin, cefazodone, cefatrizine, cefamandole, ceftiofur, cyclacillin and ampicillin:

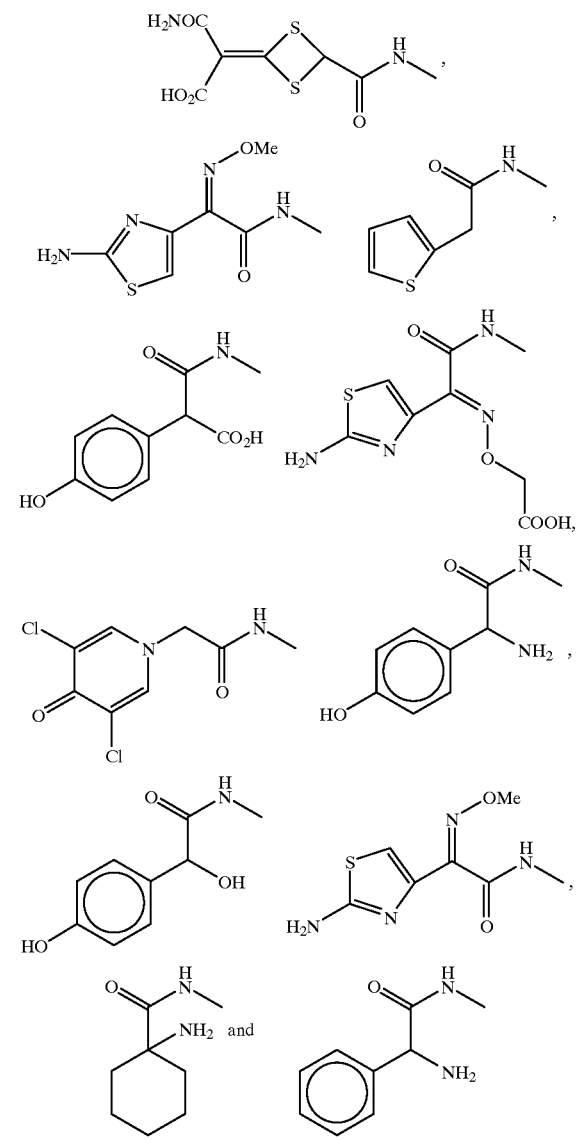

wherein Me represents methyl.

EXPERIMENTAL SECTION

General Methods

For anhydrous reactions, glassware was dried overnight in an oven at 120° C. and cooled in a desiccator over anhydrous $CaSO_4$ or silica gel. Reagents purchased from Fluka Chemical Co. Solvents, including chloroform, dichloromethane, dimethylformamide, ethyl acetate, hexanes, and pyridine were distilled over $CaH_2$ under nitrogen. Absolute ethanol was purchased from Merck and used as received. Solid magnesium sulfate (i.e., $MgSO_4$ (s)) from Aldrich, was used for drying reaction products after workup. Reactions were carried out in nitrogen atmosphere; the apparatus was evacuated and filled with dry nitrogen at least three times.

Melting points were obtained with a Büchi 510 melting point apparatus. Infrared (IR) spectra were recorded on a Beckman IR-8 spectrophotometer. The wavenumbers reported are referenced to the 1601 $cm^{-1}$ absorption of polystyrene. Proton NMR spectra were obtained on a Varian XL-300 (300 MHz) spectrometer. Chloroform-d and $D_2O$ were used as solvent; $Me_4Si$ ($\delta$ 0.00 ppm) was used as an internal standard. All NMR chemical shifts are reported as $\delta$ values in parts per million (ppm) and coupling constants (J) are given in hertz (Hz). The splitting pattern abbreviations are as follows: s, singlet; d, doublet; t, triplet; q, quartet; br, broad; m, unresolved multiplet due to the field strength of the instrument; and dd, doublet of doublets. Microanalyses were performed on a Perkin-Elmer 240-B microanalyzer. Purification on silica gel refers to gravity column chromatography on Merck Silica Gel 60 (particle size 230–400 mesh), packed in glass column (35 g of silica gel/gram of crude material). Analytical TLC was performed on precoated plates purchased from Merck (Silica Gel 60 $F_{254}$). Compounds were visualized by use of UV light, $I_2$ vapor, or 2.5% phosphomolybdic acid in ethanol with heating.

(+)-Dibenzyl 2-(cis-4-Azidomethyl-2-oxo-3-phenylacetamido-1-azetidinyl)-malonate (7)

To a solution containing (±)-6 (2.97 g, 4.99 mmol) in DMF (40 mL) was added $NaN_3$ (1.30 g, 20.0 mmol). The solution was stirred at room temperature for 48 h and then partitioned between $Et_2O$ (100 mL) and water (100 mL). The organic layer was washed with water (4×80 mL), dried over $MgSO_4$ (s), filtered, and concentrated under reduced pressure. The crude product was purified by use of column chromatography ($CHCl_3$ as eluant) to give (±)-7 (2.43 g, 4.49 mmol) as a foam in 90% yield: $^1H$ NMR ($CDCl_3$) $\delta$ 3.59 (s, 2H), 3.68–3.88 (m, 2H), 4.10–4.28 (m, 1H), 5.27 (s, 4H), 5.32 (s, 1H), 5.34 (dd, J=8.5, 5.0, 1H), 6.99 (d, J=8.5, 1H), 7.15–7.45 (m, 15H); IR ($CH_2Cl_2$) 3405, 2100, 1768, 1740, 1680 $cm^{-1}$. Anal. ($C_{29}H_{27}N_5O_6$) C, H, N.

(±)-Dibenzyl 2-(cis-4-Azidomethyl-2-oxo-3-phenylacetamido-1-azetidinyl)-2-chloromalonate (8)

To a solution of (±)-7 (2.70 g, 4.99 mmol) in $CH_2Cl_2$ (50 mL) was added $Et_3N$ (0.61 g, 6.0 mmol). Trifluoromethanesulfonyl chloride (0.86 g, 5.1 mmol) in $CH_2Cl_2$ (5.0 mL) was added dropwise to the reaction mixture at 0° C. over 5.0 min. After the mixture was warmed up to room temperature, it was concentrated to dryness and then $Et_2O$ was added. The ethereal layer was washed with water (2×50 mL), dried over $MgSO_4$ (s), and treated with charcoal. After filtration, evaporation, and purification by use of column chromatography ($CHCl_3$ as eluant), β-lactam (±)-8 (2.59 g, 4.49 mmol) was obtained in 90% yield as a foam: $^1H$ NMR ($CDCl_3$) $\delta$ 3.58 (s, 2H), 3.70–3.91 (m, 2H), 4.15–4.30 (m, 1H), 5.21 (s, 2H), 5.32 (s, 2H), 5.36 (dd, J=8.0, 5.0, 1H), 7.00 (d, J=8.0, 1H), 7.20–7.38 (m, 15H); IR ($CH_2Cl_2$) 3410, 2110, 1790, 1750, 1682 $cm^{-1}$. Anal. ($C_{29}H_{26}N_5O_6Cl$) C, H, N, Cl.

Benzyl (6RS,7SR)-3-Hydroxy-8-oxo-7-(phenylacetamido)-1,4-diazabicyclo-[4.2.0]oct-2-ene-2-carboxylate ((±)-9)

Method A: β-Lactam (±)-7 (2.70 g, 4.99 mmol) in EtOAc (80 mL) was hydrogenated under 30–35 psi of $H_2$ in the presence of Pd/C (10%, 40.0 mg, 0.0400 mmol) at room temperature for 30 min. After filtration and evaporation, the crude foam was chromatographed (EtOAc as eluant) to give (±)-9 (1.91 g, 4.69 mmol) as a foam in 94% yield: $^1H$ NMR ($CDCl_3$) $\delta$ 2.50–2.68 (br, 1H), 2.85–3.02 (br, 1H), 3.21–3.45 (m, 2H), 3.55 (s, 2H), 4.18–4.43 (m, 1H), 5.09 (dd, J=8.0, 4.5, 1H), 5.15 (s, 2H), 6.38 (d, J=8.0, 1H), 7.31–7.42 (m, 10H); IR ($CH_2Cl_2$) 3500–3200, 1787, 1740, 1725, 1680 $cm^{-1}$. Anal. ($C_{22}H_{21}N_3O_5$) C, H, N.

Method B:

β-Lactam (±)-8 (575 mg, 0.998 mmol) in EtOAc (50 mL) was hydrogenated under 30–35 psi of 1–2 in the presence of Pd/C (10%, 20.0 mg, 0.020 mmol) at room temperature for 30 min. After filtration and evaporation, the crude foam was chromatographed (EtOAc as eluant) to give (±)-9 (354 mg, 0.868 mmol) as a foam in 87% yield.

(6RS,7SR)-3-Hydroxy-8-oxo-7-(phenylacetamido)-1,4-diazabicyclo[4.2.0]-oct-2-ene-2-carboxylic Acid ((±)-10)

A solution of (±)-9 (0.41 g 1.0 mmol) in EtOH (35 mL) was hydrogenated on $PdCl_2$ (150 mg, 0.846 mmol) at 60 psi of $H_2$ at room temperature for 3.0 h. It was then filtered and concentrated under reduced pressure. The crude product was recrystallized from EtOAc to afford pure (±)-10 (0.16 g, 0.50 mmol) in 50% yield: mp 140–142° C.; $^1H$ NMR ($CDCl_3$/DMSO-$d_6$/$D_2O$) $\delta$ 3.20–3.41 (m, 2H), 3.50 (s, 2H), 4.20–4.40 (m, 1H), 5.05 (d, J=5.0, 1H), 7.30–7.58 (m, 5H); IR (nujol) 3650–3155, 1781, 1725, 1680 $cm^{-1}$. Anal. ($C_{15}H_{15}N_3O_5$) C, H, N.

Dibenzyl (5RS,6SR)-7-Oxo-6-(phenylacetamido)-1,3-diazabicyclo[3.2.0]heptane-2,2-dicarboxylate ((±)-14)

Triethylamine (0.12 g, 1.2 mmol) was added to a solution of (±)-8 (0.58 g, 1.0 mmol) in $CH_2Cl_2$ (50 mL) at 0° C. and then $H_2S$ was bubbled into the solution for 15 min. The solution was allowed to stand at room temperature for 2.0 h while evolution of $N_2$ gas was observed. The solution was purged with $N_2$ gas for 30 min, which was then washed with water (4×50 mL), dried over $MgSO_4$ (s), and concentrated under reduced pressure. The crude product was purified by use of column chromatography (EtOAc as eluant) to afford (±)-14 (0.21 g, 0.40 mmol) as a foam in 40% yield. Further elution of the column with EtOAc gave (±)-9 (61 mg, 0.15 mmol) as a foam in 15% yield. For (±)-14: $^1H$ NMR ($CDCl_3$) $\delta$ 2.85–3.29 (m, 2H), 3.31–3.46 (br, 1H), 3.53 (s, 2H), 4.29–4.52 (m, 1H), 5.31 (dd, J=8.0, 4.5, 1H), 5.20 (s, 2H), 5.21 (s, 2H), 7.16–7.46 (m, 16H); IR ($CH_2Cl_2$) 3450–3300, 1786, 1749, 1682 $cm^{-1}$. Anal. ($C_{29}H_{27}N_3O_6$) C, H, N.

Benzyl (6RS,7SR)-3-Methanesulfonyloxy-8-oxo-7-(phenylacetamido)-1,4-diazabicyclo[4.2.0]oct-2-ene-2-carboxylate ((±)-11)

To a solution containing (±)-9 (4.07 g, 9.99 mmol) and pyridine (2.80 g, 35.4 mmol) in $CH_2Cl_2$ (86 mL) was added $MeSO_2Cl$ (1.15 g, 10.0 mmol). After the solution was stirred at 15° C. for 5.0 h, it was washed with water (100 mL), dried over $MgSO_4$ (s), and concentrated under reduced pressure. Purification of the residue by use of column chromatography (EtOAc as eluant) gave (±)-11 (2.18 g, 4.50 mmol) as a foam in 45% yield: $^1H$ NMR ($CDCl_3$) $\delta$ 2.66–2.80 (br, 1H), 2.99 (s, 3H), 3.22–3.45 (m, 2H), 3.55 (s, 2H), 4.10–4.41 (m, 1H), 5.05 (dd, J=9.0, 5.0, 1H), 5.23 (s, 2H), 6.40 (d, J=9.0, 1H), 7.30–7.50 (m, 10H); IR ($CH_2Cl_2$) 3450–3250, 1788, 1750, 1730, 1680 $cm^{-1}$. Anal. ($C_{23}H_{23}N_3O_7S$) C, H, N, S.

(6RS,7SR)-3-Methanesulfonyloxy-8-oxo-7-(phenylacetamido)-1,4-diazabicyclo[4.2.0]oct-2-ene-2-carboxylic Acid ((±)-3).

A solution of (±)-11 (0.500 g, 1.03 mmol) in EtOH (50 mL) was hydrogenated with $H_2$ at 60 psi on $PdCl_2$ (150 mg, 0.846 mmol) at room temperature for 3.0 h. The solution was then filtered and concentrated under reduced pressure. Purification of the residue by use of column chromatography (EtOAc/EtOH (9:1)) gave (±)-3 (0.14 g, 0.36 mmol) in 35% yield: mp 115–117° C.; $^1$H NMR (CDCl$_3$/D$_2$O) δ 2.98 (s, 3H), 3.20–3.43 (m, 2H), 3.52 (s, 2H), 4.12–4.42 (m, 1H), 5.10 (d, J=5.0, 1H), 7.25–7.48 (m, 6H); IR (CH$_2$Cl$_2$) 3460–3100, 1787, 1710, 1700, 1680 cm$^{-1}$. Anal. ($C_{16}H_{17}N_3O_7S$) C, H, N, S.

Benzyl (6RS,7SR)-3-Trifluoromethanesulfonyloxy-8-oxo-7-(phenylacetamido)-1,4-diazabicyclo[4.2.0]oct-2-ene-2-carboxylate ((±)-12) and Benzyl (6SR,7SR)-3-Trifluoromethanesulfonyloxy-8-oxo-7-(phenylacetamido)-4-trifluoromethane-sulfonaza-1-azabicyclo[4.2.0]oct-2-ene-2-carboxylate ((±)-13)

To a solution containing (±)-9 (4.07 g, 9.99 mmol) and pyridine (2.80 g, 35.4 mmol) in CH$_2$Cl$_2$ (80 ml,) was added CF$_3$SO$_2$Cl (1.69 g, 10.0 mmol) in CH$_2$Cl$_2$ (5.0 mL). After the solution was stirred at 15° C. for 5.0 h, it was washed with water (100 mL), dried over MgSO$_4$ (s), and concentrated under reduced pressure. Purification of the residue by use of column chromatography (EtOAc as eluant) gave (±)-12 (1.62 g, 3.00 mmol) as a foam in 30% yield. Further elution of the column with EtOAc afforded (±)-13 (0.67 g, 1.0 mmol) as an oil in 10% yield.

For (±)-12: $^1$H NMR (CDCl$_3$) δ 2.96–3.10 (br, 1H), 3.24–3.48 (m, 2H), 3.54 (s, 2H), 4.21–4.49 (m, 1H), 5.04 (dd, J=9.0, 5.0, 1H), 5.25 (s, 2H), 6.48 (d, J=9.5, 1H), 7.25–7.48 (m, 10H); IR (CH$_2$Cl$_2$) 3455–3250, 1792, 1752, 1735, 1680 cm$^{-1}$. Anal. ($C_{23}H_{20}F_3N_3O_7S$) C, H, F, N, S.
For (±)-13: $^1$H NMR (CDCl$_3$) δ 3.45–3.78 (m, 2H), 3.58 (s, 2H), 4.26–4.51 (m, 1H), 5.06 (dd, J=8.0, 4.5, 1H), 5.36 (s, 2H), 6.60 (d, J=8.0, 1H), 7.30–7.50 (m, 10H); IR (CH$_2$Cl$_2$) 3350–3300, 1798, 1754, 1739, 1678 cm$^{-1}$.

(6RS,7SR)-3-Trifluoromethanesulfonyloxy-8-oxo-7-(phenylacetamido)-1,4-diazabicyclo[4.2.0]oct-2-ene-2-carboxylic Acid ((±)-4)

A solution of (±)-12 (0.54 g, 1.0 mmol) in EtOH (50 mL) was hydrogenated with H$_2$ at 60 psi on PdCl$_2$ (150 mg, 0.846 mmol) at room temperature for 3.0 h. The solution was then filtered and concentrated under reduced pressure. Purification of the residue by use of column chromatography (EtOAc/EtOH (9:1)) gave (±)-4 (135 mg, 0.300 mmol) in 30% yield: mp 100–102° C.; $^1$H NMR (CDCl$_3$/D$_2$O) δ 3.21–3.43 (m, 2H), 3.55 (s, 2H), 4.13–4.44 (m, 1H), 5.02 (d, J=5.0, 1H), 7.30–7.50 (m, 5H); IR (CH$_2$Cl$_2$) 3465–3100, 1790, 1720, 1710, 1680 cm$^{-1}$. Anal. ($C_{16}H_{14}F_3N_3O_7S$) C, H, F, N, S.

(±)-Dibenzyl-2-(cis-4-Azidomethyl-2-oxo-3-phenylacetamido-1-azetidinyl)-2-mesylmalonate (15)

To a solution containing (±)-7 (5.41 g, 9.99 mmol) and Et$_3$N (1.05 g, 10.4 mmol) in CH$_2$Cl$_2$ (80 mL) was added dropwise MeSO$_2$Cl (1.15 g, 10.0 mmol) in CH$_2$Cl$_2$ (10 mL). After the solution was stirred at 0° C. for 1.0 h, it was washed with water (100 mL), dried over MgSO$_4$ (s), and concentrated under reduced pressure. Purification of the residue by use of column chromatography (CHCl$_3$ as eluant) afforded (±)-15 (5.26 g, 8.49 mmol) in 85% yield: mp 114–115° C.; $^1$H NMR (CDCl$_3$) δ 3.39 (s, 3H), 3.61 (s, 2H), 3.69–3.95 (m, 2H), 4.15–4.30 (m, 1H), 5.12 (s, 21H), 5.13 (s, 21H), 5.35 (dd, J=8.0, 5.0, 1H), 6.98 (d, J=8.0, 1H), 7.40–7.70 (m, 15H); IR (CH$_2$Cl$_2$) 3410, 2100, 1790, 1751, 1680 cm$^{-1}$. Anal. ($C_{30}H_{29}N_5O_8S$) C, H, N, S.

Benzyl (2RS,6RS,7SR)- and (2SR,6RS,7SR)-2-Methanesulfonyl-3,8-dioxo-7-(phenylacetamido)-1,4-diazabicyclo[4.2.0]octane-2-carboxylate (Diastereoisomeric Mixture; (±)-16)

A solution of (±)-15 (3.10 g, 5.00 mmol) in EtOAc (200 mL) was hydrogenated on 10% Pd/C (40 mg, 0.041 mmol) at 30–35 psi of H$_2$ at room temperature for 1.5 h. After filtration and condensation, the crude foam was crystallized from Et$_2$O to give (±)-16 (2.19 g, 4.50 mmol) in 90% yield: mp 135–137° C.; $^1$H NMR (CDCl$_3$) δ 3.41 (s, 3H), 3.35–3.61 (m, 2H), 3.58 (s, 2H), 4.20–4.45 (m, 1H), 4.96 (dd, J=8.0, 4.5, 1H), 5.14 (s, 2H), 6.40–7.10 (br, 2H), 7.35–7.63 (m, 10H); IR (CH$_2$Cl$_2$) 3415–3405, 1791, 1745, 1682, 1668 cm$^{-1}$. Anal. ($C_{23}H_{23}N_3O_7S$) C, H, N, S.

(2RS,6RS,7SR)- and (2SR,6RS,7SR)-2-Methanesulfonyl-3,8-dioxo-7-(phenylacetamido)-1,4-diazabicyclo[4.2.0]octane-2-carboxylic Acid (Diastereo-isomeric Mixture; (±)-5) and (6RS,7SR)-3-Hydroxy-8-oxo-7-(phenylacetamido)-1,4-diazabicyclo[4.2.0]oct-2-ene-2-methylsulfone ((±)-17)

A solution of (±)-16 (0.49 g, 1.0 mmol) in EtOH (40 mL) was hydrogenated with 112 at 60 psi on PdCl$_2$ (150 mg, 0.846 mmol) at room temperature for 4.0 h. The solution )as then filtered and concentrated under reduced pressure. Purification of the residue by use of column chromatography (EtOAc as eluant) gave (±)-17 (0.18 g, 0.50 mmol) as a foam in 50% yield. Further elution of the column with a mixture of EtOAc and EtOH (4:1) afforded (±)-5 (80 mg, 0.20 mmol) in 20% yield. For (±)-5: mp 160–166° C.; $^1$H NMR (CDCl$_3$/D$_2$O) δ 3.20–3.42 (m, 2H), 3.19 (s, 3H), 3.55 (s, 2H), 4.15–4.40 (m, 1H), 5.13 (d, J=5.0, 1H), 7.23 (br s, 5H); IR (CH$_2$Cl$_2$) 3400–3120, 1780, 1700, 1680, 1670 cm$^{-1}$.
For (±)-17: $^1$H NMR (CDCl$_3$) δ 2.60–2.90 (br, 2H), 3.22–3.48 (m, 2H), 3.50 (s, 3H), 3.59 (s, 2H), 4.17–4.42 (m, 1H), 5.13 (dd, J=8.0, 4.5, 1H), 6.95 (d, J=8.0, 1H), 7.30 (br s, 5H); IR (CH$_2$Cl$_2$) 3500–3200, 1789, 1727, 1680 cm$^{-1}$. Anal. ($C_{15}H_{17}N_3O_5S$) C, H, N, S.

Antibacterial Activity Tests.

The serial broth dilution method was used to study the antibiotic activity [Pursiano, T. A.; Misiek, M.; Leitner, F.; Price, K. E. Effect of Assay Medium on the Antibacterial Activity of Certain Penicillins and Cephalosporins. *Antimicrob. Agents Chemother.* 1973, 3, 33–39]. The inocula were prepared by use of the heart infusion broth (Difco Laboratories) to make $10^{-4}$ dilutions of the overnight cultures. Tubes of the seeded antibiotic-containing media were incubated at 37° C. for 20 h. The lowest concentration of antibiotic that prevented visible growth of microorganisms was then determined.

What is claimed is:

1. An isodethiaazacephem derivative having the following formula (I):

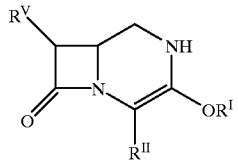

wherein $R^I$ is hydrogen or —$SO_2R^{III}$;

$R^{II}$ is —$CO_2R^{IV}$ or —$SO_2R^{III}$;
wherein $R^{III}$ is a hydrogen, C1–C6 alkyl, aralkyl having a total carbon number of 7–12, aryl, or a halogenated C1–C6 alkyl; and $R^{IV}$ is a hydrogen, C1–C6 alkyl, aralkyl having a total carbon number of 7–12 or aryl; and $R^V$ is a substituted acetamido radical selected from the group consisting essentially of phenylacetamido,

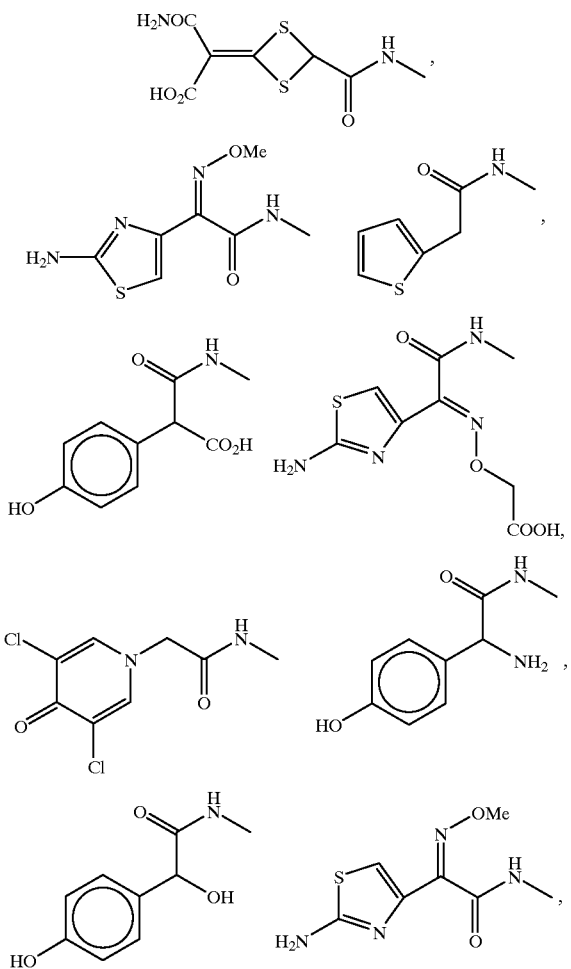

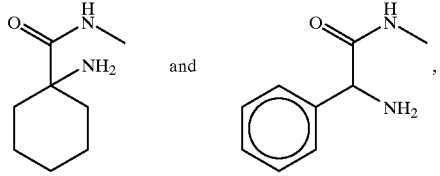

wherein Me represents methyl.

2. The isodethiaazacephem derivative according to claim 1, wherein $R^I$ is —$SO_2R^{III}$.

3. The isodethiaazacephem derivative according to claim 2, wherein $R^{III}$ is a C1–C6 alkyl or a halogenated C1–C6 alkyl.

4. The isodethiaazacephem derivative according to claim 3, wherein $R^{III}$ is methyl.

5. The isodethiaazacephem derivative according to claim 3, wherein $R^{III}$ is —$CF_3$.

6. The isodethiaazacephem derivative according to claim 1, wherein $R^{II}$ is —$CO_2R^{IV}$.

7. The isodethiaazacephem derivative according to claim 2, wherein $R^{II}$ is —$CO_2R^{IV}$.

8. The isodethiaazacephem derivative according to claim 3, wherein $R^{II}$ is —$CO_2R^{IV}$.

9. The isodethiaazacephem derivative according to claim 4, wherein $R^{II}$ is —$CO_2R^{IV}$.

10. The isodethiaazacephem derivative according to claim 5, wherein $R^{II}$ is —$CO_2R^{IV}$.

11. The isodethiaazacephem derivative according to claim 6, wherein $R^{IV}$ is hydrogen.

12. The isodethiaazacephem derivative according to claim 7, wherein $R^{IV}$ is hydrogen.

13. The isodethiaazacephem derivative according to claim 8, wherein $R^{IV}$ is hydrogen.

14. The isodethiaazacephem derivative according to claim 9, wherein $R^{IV}$ is hydrogen.

15. The isodethiaazacephem derivative according to claim 10, wherein $R^{IV}$ is hydrogen.

16. The isodethiaazacephem derivative according to claim 11, wherein $R^V$ is phenylacetamido.

17. The isodethiaazacephem derivative according to claim 12, wherein $R^V$ is phenylacetamido.

18. The isodethiaazacephem derivative according to claim 13, wherein $R^V$ is phenylacetamido.

19. The isodethiaazacephem derivative according to claim 14, wherein $R^V$ is phenylacetamido.

20. The isodethiaazacephem derivative according to claim 15, wherein $R^V$ is phenylacetamido.

21. An antibacterial pharmaceutical composition a therapeutically effective amount of the isodethiaazacephem derivative as defined in any one claim of claims 1–20 or a pharmaceutically effective acceptable salt thereof, as an active ingredient, in admixture with a pharmaceutically acceptable carrier or diluent for the active ingredient.

22. An isodethiaazacepham derivative having, the following, formula (II):

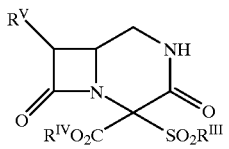

wherein $R^{III}$ is a hydrogen, C1–C6 alkyl, aralkyl having a total carbon number of 7–12, aryl, or a halogenated C1–C6 alkyl;
$R^{IV}$ is a hydrogen, C1–C6 alkyl, aralkyl having a total carbon number of 7–12 or aryl; and
$R^{V}$ is a substituted acetamido radical selected from the group consisting essentially of phenylacetamido, phenoxyacetamido,

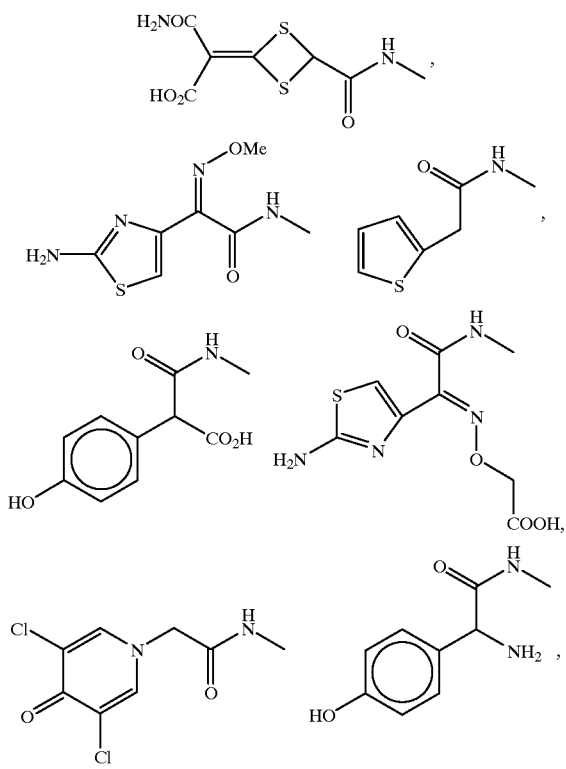

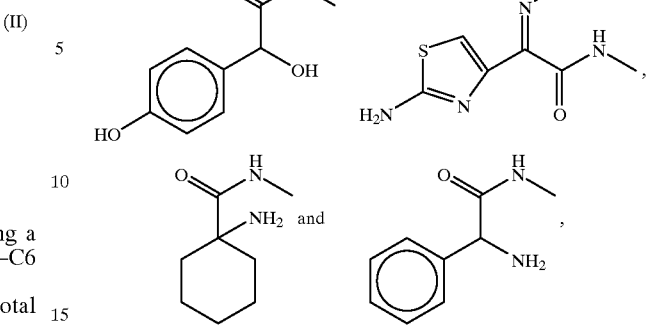

wherein Me represents methyl.

23. The isodethiaazacepham derivative according to claim 22, wherein $R^{III}$ is a C1–C6 alkyl.

24. The isodethiaazacepham derivative according to claim 23, wherein $R^{III}$ is methyl.

25. The isodethiaazacepham derivative according to claim 22, wherein $R^{IV}$ is hydrogen.

26. The isodethiaazacepham derivative according to claim 23, wherein $R^{IV}$ is hydrogen.

27. The isodethiaazacepham derivative according to claim 24, wherein $R^{IV}$ is hydrogen.

28. The isodethiaazacepham derivative according to claim 22, wherein $R^{V}$ is phenylacetamido.

29. The isodethiaazacepharn derivative according to claim 23, wherein $R^{V}$ is phenylacetamido.

30. The isodethiaazacepham derivative according to claim 24, wherein $R^{V}$ is phenylacetamido.

31. The isodethiaazacepham derivative according to claim 25, wherein $R^{V}$ is phenylacetamido.

32. The isodethiaazacepham derivative according to claim 26, wherein $R^{V}$ is phenylacetamido.

33. The isodethiaazacepham derivative according to claim 27, wherein $R^{V}$ is phenylacetamido.

34. An antibacterial pharmaceutical composition a therapeutically effective amount of the isodethiaazacepham derivative as defined in any one claim of claims 22–33 or a pharmaceutically effective acceptable salt thereof, as an active ingredient, in admixture with a pharmaceutically acceptable carrier or diluent for the active ingredient.

* * * * *